(12) United States Patent
Ning et al.

(10) Patent No.: US 6,703,000 B2
(45) Date of Patent: *Mar. 9, 2004

(54) CONFECTIONERY COMPOSITIONS

(75) Inventors: Ji Ning, Science Park (CN); Thomas Mark Lawlor, Ashford (GB); Zhu Long, Science Park (CN)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/146,247

(22) Filed: May 15, 2002

(65) Prior Publication Data

US 2003/0049303 A1 Mar. 13, 2003

Related U.S. Application Data

(60) Provisional application No. 60/291,177, filed on May 15, 2001.

(51) Int. Cl.⁷ .................................................. A61K 7/26
(52) U.S. Cl. ............................. 424/58; 424/49; 424/50; 424/51; 424/52; 424/53; 424/54; 424/55; 424/56; 424/57; 424/48; 424/440; 426/3; 426/4; 426/5; 426/6; 426/660
(58) Field of Search ............................. 424/49–58, 48, 424/440; 426/3–6, 660

(56) References Cited

U.S. PATENT DOCUMENTS 5,741,138 A  4/1998  Rice et al.

FOREIGN PATENT DOCUMENTS

| | | |
|---|---|---|
| CN | 1060012 A | 9/1991 |
| CN | 1069190 A | 2/1993 |
| CN | 1094895 | 11/1994 |
| CN | 1096699 | 12/1994 |
| CN | 1111097 | 11/1995 |
| CN | 1141161 | 1/1997 |
| DE | 4221103 | 6/1992 |
| EP | 1013261 | 6/2000 |
| EP | 1046398 | 10/2000 |
| JP | 10-90124 | 10/1987 |
| JP | 3-77817 | 4/1991 |
| JP | 3-284625 | 12/1991 |
| JP | 57-85319 | 12/1992 |
| JP | 5-262630 | 10/1993 |
| JP | 6-40834 | 2/1994 |
| JP | 6-40868 | 2/1994 |
| JP | 9-110687 | 4/1997 |
| JP | 10-152426 | 6/1998 |
| JP | 10-182388 | 7/1998 |
| JP | 11-228368 | 8/1998 |
| JP | 10-257856 | 9/1998 |
| JP | 11-302142 | 11/1999 |
| JP | 2000-189060 | 7/2000 |
| JP | 2000-212094 | 8/2000 |
| JP | 2000-239136 | 9/2000 |
| WO | WO 95/00038 | 1/1995 |
| WO | WO 96/28135 | 9/1996 |
| WO | WO 98/06377 | 2/1998 |
| WO | WO 99/44436 | 9/1999 |
| WO | WO 99/44440 | 10/1999 |
| WO | WO 00/06127 | 2/2000 |
| WO | WO 01/17494 | 3/2001 |
| WO | WO 01/82922 | 11/2001 |

Primary Examiner—Frederick Krass
(74) Attorney, Agent, or Firm—Betty J. Zea; Emelyn Deleon Hiland

(57) ABSTRACT

A confectionery composition comprising:
(i) an effective amount of a natural plant extract selected from tea, gold thread, honeysuckle, magnolia extracts and mixtures thereof;
(ii) an oral care active selected from the group consisting of anti-calculus agents; anti-plaque agents; fluoride ion source; desensitising agents; oral malodour control agents; H2 antagonists; and mixtures thereof;
(iii) less than about 10% water; and
(iv) a suitable confectionery carrier material.

17 Claims, No Drawings

CONFECTIONERY COMPOSITIONS

CROSS REFERENCE TO RELATED APPLICATION

This application claims the benefit of U.S. Provisional Application No. 60/291,177 filed May 15, 2001.

FIELD OF THE INVENTION

The present invention relates to confectionery compositions that comprise an effective amount of a natural plant extract selected from honeysuckle extract, green tea extract, gold thread extract and magnolia extract and mixtures thereof, an oral care active selected from the group consisting of anti-calculus agents; anti-plaque agents; fluoride ion source desensitising agents; oral malodour control agents; H2 antagonists; and mixtures thereof and wherein the confectionery composition comprises less than 10%, by weight of the composition, water. Preferably this invention relates to non cariogenic or so called "sugar free" confectionery compositions. In particular this invention relates to compositions that have improved ability to combat halitosis of a subject. Compositions of the present invention are suitable for use by humans or animals.

BACKGROUND OF THE INVENTION

Oral malodour or halitosis, which is commonly referred to as bad breath, is the result of volatile sulphur compounds, carboxylic acids and amines building up in the oral cavity. The malodourous compounds are generated primarily through putrefactive action of oral micro organisms on sulphur containing amino acids, peptones or proteins found in the mouth. Such micro-organisms are readily available in saliva and dental plaque and may be derived from proteinaceous food particles trapped between the teeth, in the gingival crevice or adhering to the mucous membranes and the irregular surface of the tongue as well as exfoliated oral epitheleum, food debris and the like. In addition oral malodour may be the result of poor oral hygiene, digestive system problems, disease, diet or a combination of any of these factors. Not only is oral malodour unpleasant but its presence can be indicative of poor oral hygiene and can also be one of the first signs of some more severe underlying problems. This is because the build up of putrid matter which causes malodour can also lead to the formation of plaque, the origin of dental caries, gingivitis and dental calculus. Regular brushing of teeth can help to minimise oral malodour. However, even regular brushing is not sufficient to remove all of the food and oral bacteria deposits that adhere to the oral surfaces and, in severe cases it is unable to eliminate oral malodour.

There is currently a movement in the oral care industry to encourage consumers to use dental hygiene products throughout the day and to brush their teeth more often. However, this is at best inconvenient and is often not possible. As such significant developmental effort has been focused towards developing oral care products in forms which are portable, which can be used several times a day, particularly after eating and which provide anti-plaque and anti-calculus benefits comparable to those obtained by regular brushing with dentifrice. It is hoped that such a product will improve the oral hygiene of consumers. In addition, such a product would make it easier to provide good oral hygiene to children and pets where it is not always easy to regularly brush the teeth.

Confectionery compositions which are popular with both children and adults alike and which are retained in the oral cavity for substantial periods of time during consumption, would seem to make an ideal product form for a portable oral care product. Furthermore chewing gums have many benefits as a portable oral care form since they remain within the oral cavity for significant periods of time, typically 20 minutes or longer. The art of the development and manufacture of a wide range of confectionery compositions is well known. However, the high sugar content of such confectionery compositions has been recognised as a contributory factor in poor dental health. Developments have been made to produce "sugar free", or non cariogenic, confectionery which retain their organoleptic properties but which do not contribute to the formation of dental plaque. More recently research has turned to developing confectionery compositions, particularly "sugar free" confectionery compositions, particularly chewing gum compositions, which comprise one or more oral care agents. One such example is WO 99/44436 which discloses coated chewing gum compositions which comprise materials with known oral care benefits. There exists a need therefore for a wide range of confectionery compositions which have oral malodour benefits. In addition there is a need for such compositions to be able to deliver a wide range of oral care benefits including more effective oral malodour control benefits thus providing a composition which is able to deliver a wide range of oral care benefits.

To date oral malodour products have been formulated to comprise a wide range of materials that kill the oral bacteria contributing to the oral malodour. Such materials include agents such as triclosan, stannous fluoride, metal cations, chlorhexidine, quaternary ammonium salts and camphorated parachlorophenol. However, these materials can be harsh, and can only be dosed in limited daily amounts and as such are not necessarily suitable for use in a product to be used several times a day. In some cases they may also cause undesirable side effects such as staining, altered taste etc.

More recently trends have been directed towards the use so called natural materials, especially extracts. Herbal curry plant extract has been disclosed in JP 10-182,388 for combating halitosis; cranberry extract has been disclosed in WO 96/28135 for is antimicrobial properties; U.S. Pat. No. 5,741,138 discloses oral compositions comprising gold thread and honeysuckle extracts; and DE 4,221,103 discloses compositions comprising a wide range of herbal extracts for oral hygiene. Polyphenols have been identified as an important active in a wide range of herbal extracts. Examples of polyphenol disclosures include EP 1,046,398 which discloses the use of vegetable polyphenols for treatment of gingivitis; JP 2000-239,136 which discloses the use of *Perilla ocimodes* polyphenol for treatment of caries and periodontal disease; CN 1,141,161 which discloses a health care gargle for oral cleansing comprising polyphenol; JP 9-110,687 which discloses anti-cariogenic and anti-periodontis compositions comprising polyphenols; JP 10-90124 which discloses compositions comprising polyphenols for anti-plaque and anti-periodontis activity; JP 3-284,625 which discloses oral compositions comprising tea leaf extracts; and JP 3-077,817 which discloses mouth wash compositions comprising tea polyphenol for prevention of tooth decay. Furthermore the use of polyphenols has also been disclosed for oral deodorising benefits including WO 01/17494 which discloses dentifrice compositions comprising tea polyphenols; US/PCT/00/11258 which discloses dentifrice compositions comprising polyphenol herbal extracts; and EP 1,013,261 which discloses a spray liquid comprising polyphenol for the masking of halitosis. Whilst the teachings of the prior art are directed towards dentifrice and mouth wash compositions comprising polyphenol materials there remains a need to understand how to stably formulate a wide range of confectionery compositions comprising such materials with improved oral malodour control benefits.

Turning to the confectionery art there are isolated disclosures of compositions comprising polyphenol extracts. These include JP 2000-189,060 which discloses gelatine compositions comprising polyphenol for the removal of teeth staining; JP 10-257856 which discloses a chewing gum composition comprising polyphenol for the prevention of influenza; JP 2000-212,094 which discloses lozenges comprising green tea extract for treating pharyngitis; CN 1,094,895 and CN 1,096,699 which disclose chewing gums comprising magnolia bark extract; CN 1,111,097 which discloses a chewing gum compositions comprising green tea extract; JP 11-302,142 which discloses food stuffs comprising grape, tea or blueberry polyphenol extract; and WO 99/44440 which discloses a food composition comprising tea polyphenol for the prevention of periodontis. However such compositions usually comprise very low levels of extract, are often unstable and are of limited oral care benefit. There are no teachings as to how to develop a wide range of confectionery products which not only have oral malodour benefits but which also comprise one or more further oral care active such that they have additional oral hygiene benefits. Thus there remains a need for a portable oral care composition that is able to provide efficacious breath freshness whilst also delivering against other oral health benefits.

Surprisingly, it has now been found that, when a confectionery composition is prepared which comprises an effective amount of a natural plant extract from tea, gold thread, magnolia or honeysuckle; one or more further oral care actives and less than 10% water, that a composition is obtained which not only delivers effective oral malodour benefits but which also provides one or more further oral care benefits. Furthermore, by formulating the product with less than about 10% water the confectionery compositions and the extracts remain resulting in compositions that do not degrade or discolour over time. Finally by preparing a wide range of confectionery forms, portable oral care, which provides comparable benefits to frequent brushing, has been developed which is easily administered to pets and children.

While not wishing to be bound by theory it is believed that the polyphenol components of the named extracts complex with, react with, or oxidise the volatile malodour compounds resulting in a reduction of perceived malodour. Unlike metal cations, the polyphenols are retained in the oral cavity for longer periods of time thus resulting in improved oral malodour benefits. Furthermore it is believed that they may act to reduce the activity of the oral malodour causing microbes. It is believed that by carefully selecting extracts, which comprise high levels of polyphenol components, that more effective malodour control is achieved. When used in addition with a further oral care active both basic and complex synergistic effects can be noted. For example, if the extract is used in addition with a desensitising agent eg potassium nitrate, the overall oral benefits experienced are those of both agents singly eg malodour reduction and desensitisation. This is an example of basic synergy. However, more complex synergistic benefits can also be noted. For example if polyphenol is used in conjunction with another anti-plaque agent the action of the polyphenol in disrupting the cell membrane of the bacteria can make the bacteria themselves more susceptible to the further anti-plaque agent thus resulting in a greater plaque reduction than would be seen with either active alone.

It is an object of the present invention to provide a wide range of confectionery compositions with oral malodour control benefits, suitable for use by adults, children and pets. It is a further object of this invention to provide confectionery compositions which maximise the oral hygiene benefits by comprising one or more further oral care actives and enhancing the synergistic action between these actives. Finally it is an object of this invention to develop confectionery compositions which remain stable over time despite comprising extracts and actives which are known to be unstable during storage. These and other objects of the present invention will become readily apparent from the detailed description that follows.

SUMMARY OF THE INVENTION

The present invention relates to a confectionery composition comprising:
 (i) an effective amount of a natural plant extract selected from tea, gold thread, honeysuckle, magnolia extracts or mixtures thereof;
 (ii) an oral care active selected from the group consisting of anti-calculus agents; anti-plaque agents; fluoride ion source; desensitising agents; oral malodour control agents; H2 antagonists; and mixtures thereof;
 (iii) less than about 10% water; and
 (iv) a suitable confectionery carrier material.

DETAILED DESCRIPTION OF THE INVENTION

All percentages and ratios used herein are by weight of the total composition and all measurements made are at 25° C., unless otherwise designated.

All documents cited are, in relevant part, incorporated herein by reference; the citation of any document is not to be construed as an admission that it is prior art with respect to the present invention.

The term "safe and effective amount" as used herein means an amount of a compound, component, or composition sufficient to significantly induce a positive benefit, but low enough to avoid serious side effects, i.e. to provide a reasonable benefit to risk ratio, within the scope of sound medical judgement.

The term "orally active" as used herein means a material that provides either a cosmetic, prophylactic or therapeutic benefit within the oral cavity.

The term "confectionery" as defined herein means a solid, gum, gum-like, or glassy composition optionally having a liquid centre filling and/or optionally coated which comprises greater than about 25% sugar or sugar alcohol. Such compositions usually have a sweet taste. Examples of confectionery products include, but are not limited to, breath mints, low boiled candy, hard boiled candy, chewing gum, coated candy, lozenges, oral pasta, pressed mints, throat drops and the like.

The term "chewing gum" as defined herein means a confectionery composition which is suitable for chewing and which comprises 2% or greater, by weight of the composition, of elastomer.

The term "elastomer" as defined herein means a non-digestible polymeric material, or mixture of materials, such as the materials typically used in chewing gum compositions.

The term "crunchy" as defined herein means that the product has a texture such that has a firm and slightly gritty texture and which produces a slight cracking noise upon consumption. It is preferred that the compositions have a texture of granulated sugar.

Active and other ingredients useful herein may be categorised or described herein by their cosmetic and/or therapeutic benefit or their postulated mode of action. However, it is to be understood that the active and other ingredients useful herein can in some instances provide more than one therapeutic and/or cosmetic benefit or operate via more than one mode of action. Therefore, classifications herein are made for the sake of convenience and are not intended to limit an ingredient to the particularly stated application or applications listed.

The elements of the compositions and methods of the present invention are described in more detail below.

Natural Extract

Compositions of the present invention comprise an effective amount of a natural plant extract obtained from the tea, honey suckle, gold thread, magnolia plants or mixtures thereof. More preferably the extract is obtained from tea or from magnolia. Even more preferably the extract is obtained from magnolia. It is believed that the active component of the extracts is the polyphenol materials. As used herein the term "polyphenol" is defined to mean a chemical compound which comprises more than one phenol group, preferably greater than two phenol groups and more preferably greater than three phenol groups. As used herein the term "phenol group" is defined to mean an aromatic six member carbon ring to which is bonded at least one alcohol group. Extracts suitable for use in compositions of the present invention preferably comprise greater than about 1%, preferably greater than about 5%, more preferably greater than about 10% and most preferably greater than about 15%, by weight of the extract, polyphenol material. The extract may comprise up to 100% polyphenol material. The preferred and highly preferred extracts are chosen because they comprise particular types of polyphenols or higher levels of polyphenol materials.

The tea extract is preferably that obtained from green tea, even more preferably from *Camellia sinesis* L. The active components are believed to be the polyphenol catechines including catechin, epocatechin, epigallocatechin, epicatchin gallate, gallocatechin and epigallocatechin. It is preferred that the tea extract comprises greater than about 5%, preferably greater than about 10%, by weight of the extract, catechin. Furthermore it is believed that the tea polyphenol of 85% purity is the most effective polyphenol. This is preferred over higher grade tea polyphenol due to the higher levels of vitamins, tannic acid, chlorogenic acid etc present in the extract.

The gold thread extracts are obtained from one or more of the following plant families Annonaceae, Berberidaceae, Menispermaceae, Papaveraceae, Ranunculaceae, Rutaceae, Zingiberaceae, Nadina, Mahonia, Thalictrum spp. The active polyphenol is believed to be berberine. The honeysuckle (*Lonicera ceprifolium*) extracts are obtained from the flower of the honeysuckle plant. The active polyphenol materials in the honeysuckle extract are believed to be the chlorogenic acid and/or lutenolin flavanoids.

The magnolia extract, which is the highly preferred extract for use herein, is obtained from SiChuan *Magnolia Officinalis*, a natural chinese herb. The active components are believed to be the polyphenol materials magnolol, honokiol, tetrahydromagnolol, tetrahydrohonokiol and mixtures thereof; preferably magnolol and honokiol and mixtures thereof and more preferably magnolol. These polyphneol materials have been found to be more efficacious than those from the other extracts disclosed herein. It is preferred that the magnolia extract for use herein comprises greater than about 10%, preferably greater than about 20% or more preferably greater than about 30%, and up to 100%, by weight of the extract, of one or more of the magnolol, honokiol, tetrahydromagnolol, tetrahydrohonokiol materials.

Extracts such as these can be obtained from a wide variety of suppliers. One such supplier is East Earth Herb Inc. Eugene, Oreg., USA and Plantextrakt, Vestenbergsgreuth, Germany.

Extracts suitable for use in the present invention can be obtained from any part of the plant including the leaf, stem, bark, pulp, seed, flesh, juice, root and mixtures thereof. It is preferred that the extract is obtained from the leaf, pulp and seed, more preferably from the leaf, flower or bark.

The extracts for use in the present invention can be obtained from the plant material by a variety of different methods. These include pressing, extraction, distillation, and mixtures thereof. It is preferred that extracts used herein are obtained by solvent extraction, including super critical fluid extraction, preferably solvent extraction using solvents selected from the group consisting of alcohols, water, acetone, ethyl acetate, glycerol, diethyl ether, propylene glycol and mixtures thereof, preferably the solvent is selected from the group consisting of water, alcohols, glycerol, propylene glycol and mixtures thereof.

The polyphenol extracts are safe and suitable for use for humans and pets. It is preferred that compositions of the present invention comprise from about 0.0001% to about 30%, preferably from about 0.001% to about 15%, more preferably from about 0.01% to about 10%, even more preferably from about 0.1% to about 5% and most preferably from about 0.25% to about 3%, by weight of the composition, of extract.

Compositions of the present invention may optionally comprise zinc phytate in combination with natural extracts comprising polyphenols. The zinc phytate is believed to enhance the polyphenol breath protection efficacy and increase the stability of the polyphenol extract. It may also independently product breath protection, anti-plaque protection and anti-bacterial efficacy. Compositions of the present invention preferably comprise from about 0.1% to about 10%, more preferably from about 0.5% to about 5% and most preferably from about 1% to about 3%, by weight of the composition, of zinc phytate.

Polyphenol extracts for use in the present invention can optionally be encapsulated. Such encapsulation can have several benefits including stabilising the polyphenols in formula, and can provide for controlled release mechanisms. Encapsulation can be in the form of vesicles or lipsomes with unilamellar, bilamellar or multilamellar structures. Such encapsulates can be formed by the use of emulsifying agents, fatty acids eg lecithin. Encapsulation can also be made using compounds that complex the polyphenols such as cyclodextrin. Similarly polyphenols can be adsorbed within inorganic structures such as silica shell, zeolites.

The polyphenol herbal extracts deliver oral health benefits due to their ability to inhibit the growth of certain bacteria eg *S. mutans, P. ginigvalis* and *F. nucleartum* in both low and high concentrations. These bacteria are commonly acknowledged to be among the main sources of oral diseases and breath malodour. The extract itself is considered to have anti-bacterial efficacy when it displays a minimum inhibitory concentration (MIC) of less than 20,000 ppm, preferably less than 10,000 ppm, and more preferably less than 5,000 ppm vs one or more of the above bacteria. Furthermore no proliferation of said bacteria should occur in the presence of greater than or equal to 20,000 ppm of extract under conditions suitable for growth of said bacteria. The MIC level is measured by standard techniques that are well known to one skilled in the art.

Oral Care Active

Compositions of the present invention comprise an oral care active selected from the group consisting of anti-calculus agents; anti-plaque agents; fluoride ion source; desensitising agents; oral malodour control agents; H2 antagonists; and mixtures thereof. Preferably the oral care active is selected from the group consisting of anti-calculus agents; the group of anti-plaque agents; the group of desensitising agents; oral malodour control agents; more preferably the oral care active is an anti-calculus agent; more preferably the oral care active is polyphosphate. It is not intended that the actives listed in groups below are mutually exclusive and a single active may be included in compositions of the present invention to have several effects. It is highly preferred that the oral care active is a solid.

Compositions of the present invention preferably comprise from about 0.01% to about 50%, more preferably from about 0.1% to about 15%, even more preferably from about 0.25% to about 10%, and most preferably from about 0.5% to about 7%, by weight, of oral care active.

Anti-Calculus Agents: Anti-calculus agents known for use in dental care products include phosphate, pyrophosphate, polyphosphate, phosphonate, polyphosphonate and mixtures thereof. Pyrophosphates are among the best known for use in dental care products. The pyrophosphate salts useful in the present compositions include the dialkali metal pyrophosphate salts, tetra-alkali metal pyrophosphate salts and mixtures thereof in their unhydrated as well as hydrated forms are the preferred species. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) and mixtures thereof.

Polyphosphates are the highly preferred anti-calculus agents. Compositions of the present invention preferably comprise greater than about 1%, preferably from about 1.5% to about 50%, more preferably from about 2% to about 15%, even more preferably from about 3% to about 12%, and most preferably from about 5% to about 10%, by weight, of polyphosphate salt. Polyphosphate is a widely used term which relates to phosphate anions which have been polymerised by dehydration to form a polymer of the phosphate anion. The polyphosphates can exist as linear or cyclic materials or mixtures thereof. It is preferred that the polyphosphates are linear materials comprising only low levels of cyclic materials. Polyphosphates are also characterised by the average chain length of the polymer. For the purposes of this invention the polyphosphates referred to are those with an average anion chain length of 3 or greater. It is preferred that the polyphosphates have an average anion chain length of from about 3 to about 40, preferably of from about 6 to about 30; more preferably of from about 10 to about 25 and even more preferably of from about 18 to about 25, and mixtures thereof. Furthermore polyphosphates exist as salts. It is preferred that the polyphosphate is an alkali metal salt or mixtures thereof, preferably a sodium or potassium salt or mixtures thereof and more preferably a sodium salt. Polyphosphates with an average chain length of greater than four usually occur as glassy materials. As defined herein a "glassy" material is one which is amorphous. Preferred in this invention are the linear "glassy" polyphosphates having the formula:

$$XO(XPO_3)_nX$$

wherein X is sodium, potassium, or ammonium hydrogen and n averages greater than or equal to 6 or mixtures thereof. Such polyphosphates are manufactured by FMC Corporation and are commercially known as Sodaphos (n≈6), Hexaphos (n≈13), and Glass H (n≈21). Hexaphos and Glass H are preferred with Glass H being the most preferred polyphosphate. These polyphosphates may be used alone or in combination. A broad range of phosphates and their sources are described in Kirk & Othermer, *Encyclopedia of Chemical Technology*, Fourth Edition, Volume 18, Wiley-Interscience Publishers (1996), incorporated herein by reference in its entirety, including all references incorporated into Kirk & Othermer. Polyphosphates and pyrophosphate salts have been found to have a synergistic effect when combined in a composition with an anti-microbial extract. It is believed that this is as a result of their mechanisms of action. The phosphate salts act in part to prevent the attachment of plaque to the teeth. At the same time the extract is working to reduce the level of plaque in the mouth. It is believed that the extract is able to be more effective when the oral microbes are not attached to the surface of the teeth. Thus, by combining these two materials surprisingly better effects are achieved than would be achieved by using either alone.

Additional anti-calculus agents include polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Bendict, Bush and Sunberg on Jul. 11, 1989; ethylenediaminetetraacetic acid as disclosed in British Patent No 490,384 date Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973; U.S. Pat. No. 3,988,443 issued to Ploger, Schmidt-Dunker and Gloxhuber on Oct. 26, 1976 and U.S. Pat. No. 4,877,603 issued to Degenhardt and Kozikowski on Oct. 31, 1989.

Anti-plaque Agents: Anti-plaque agents include anti-plaque agents and flouride ion sources. Anti-plaque agents are any substances which inhibit the accumulation of bacterial deposits on the surfaces of the oral cavity. Examples include xylitol and other anti-microbial agents. The inhibition effects of the xylitol on oral microbes is able to have better effect when used in conjunction with an extract since the extract is also acting to disable the microbes.

Fluoride Ion Source: Application of fluoride ions to dental enamel serves to protect teeth against decay. A wide variety of fluoride ion yielding materials can be employed as sources of soluble fluoride in the present compositions. Examples of suitable fluoride ion yielding materials are found in U.S. Pat. No. 3,535,421, Oct. 20, 1970 issued to Briner et al and U.S. Pat. No. 3,678,154 Jul. 18, 1972 issued to Widder et al. Preferred fluoride ion sources for use herein include sodium fluoride, potassium fluoride, stannous fluoride, ammonium fluoride and mixtures thereof. Sodium fluoride is particularly preferred. Preferably the present composition provide from about 50 ppm to about 10,000 ppm, more preferably from about 100 ppm to about 3000 ppm of fluoride ions. Again it is believed that when used in conjunction with one of the natural extracts claimed herein the fluoride ions are able to have better effect since there has been a reduction in plaque and microbe activity in the oral cavity due to the anti-bacterial effect of the extract.

Desensitising Agents: Desensitising agents, or anti-pain agents, can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc. Analgesics, including low levels of non-steroidal anti-inflammatory agents, such as ketorolac, flurbinprofen, ibuprofen, naproxen, indomethacin, aspirin, ketoprofen, piroxicam and meclofenamic acid, may also be used as desensitising agents.

Oral Maldour Control Agents: Oral malodour control agents include a wide variety of materials. The most commonly used are antimicrobial agents can also be present in the oral care compositions or substances of the present invention. Such agents may include, but are not limited to, 5-chloro-2-(2,4-dichlorophenoxy)-phenol, commonly referred to as triclosan, and described in the Merck Index, $11^{th}$ Edition, (1989), pp1529 (entry no 9573) in U.S. Pat. No. 3,506,720, and in European Patent Application No 0,251, 591 of Beecham Group, Plc, published Jan. $7^{th}$, 1988; phthalic acid and its salts including, but not limited to those disclosed in U.S. Pat. No. 4,994,262 published Feb. $19^{th}$, 1991, preferably magnesium mono-potassium phthalate, chlorhexidine (Merck Index, no 2090); alexidine (Merck Index, no 222); hexetidine (Merck Index, no 4624); sanguinarine (Merck Index, no 8320); benzalkonium chloride (Merck Index, no 1066); salicylanilide (Merck Index, no 8299); domiphen bromide (Merck Index, no 3411); cetylpyridinium chloride (CPC) (Merck Index, no 2024); tetradecylpyridinium chloride (TPC); N-tetradecyl-4-ethylpyridinium chloride (TDEPC); octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; methyl salicyclate; and mixtures of all of the above.

Metal Cations are also commonly used as anti-bacterial agents. The metal cation can be selected from any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

A wide variety of metal cation salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles. Examples of salts that are suitable for use herein include acetate, ammonium sulphate, bromide, chloride, chromate, citrate, dithionate, fluorosilicate, tartrate, fluoride, formate, iodide, nitrate, phenol sulphate, salicyclate, sulphate, gluconate, succinate, glycerophosphate, lactate and mixtures thereof; preferred are acetate, bromide, chloride, citrate, dithionate, tartrate, fluoride, formate, iodide, nitrate, sulphate, gluconate, succinate, lactate and mixtures thereof; and more preferred are acetate, chloride, citrate, sulphate, gluconate, succinate, lactate and mixtures thereof. If stannous chloride is used it may be advantageous to premix the stannous chloride with sodium gluconate prior to incorporating the salt in the composition since this can help to stabilise the stannous ions.

When a metal cation is incorporated into compositions of the present invention, which additionally comprise polyphosphate, the additional benefit of reducing the astringency of the metal cations within the composition is obtained thus improving the taste. In order to maximise this benefit it is preferred that the molar ratio of polyphosphate anion to the total level of orally active metal cation should be in the range of from about 10:1 to about 1:1, preferably from about 5:1 to about 1:1, preferably from about 3:1 to about 1:1. As used herein the term "polyphosphate anion" refers to a single anion regardless of chain length. The level of polyphosphate anion should be calculated by assuming that all of the polyphosphate material has the chain length of the average chain length of the material as quoted by the manufacturer. Compositions of the present invention preferably comprise from about 0.001% to about 5%, preferably from about 0.01% to about 2%, more preferably from about 0.1% to about 1% and most preferably from about 0.1% to about 0.5%, by weight of the composition, of metal salt comprising the orally active metal cation.

It is believed that the natural extracts and metal cations can work in synergy if used together to provide an enhanced oral malodour effect than would be achieved by using the materials individually. Whilst not wishing to be bound by theory it is believed that this effect is caused by the action of the materials on the microbes in the oral cavity which help to perpetuate malodour. It is believed that the extracts disrupt the cell membrane thus increasing their porosity. This enables a greater number of the metal cations to pass into the cell cytoplasm thus enhancing the disruptive effect. This results in a greater reduction in the organisms than would be seen by use of either material alone. Again it is believed that this activity is further enhanced if a mixture of more than one metal cation is used.

A further group of natural extracts which are useful for their oral malodour control benefits include extracts obtained from the seed or pulp of the plant, preferably from the seed. The extracts are preferably obtained from the plant group consisting of bergamot, grape, grapefruit, orange, lemon, tangerine, mandarin, satsuma, clementine, lime, and mixtures thereof; preferably from grape, grapefruit and mixtures thereof. It is preferred that compositions of the present invention comprise from about 0.1% to about 5% and preferably from about 0.25% to about 3%, by weight of the composition, of antibacterial seed or pulp extract.

The following essential oils are also known to have anti-microbial activity and are therefore optionally used in compositions of the present invention. These oils include thymol, geraniol, carvacrol, hinokitiol, eucalyptol, catechol (particularly 4-allyl catechol) and mixtures thereof.

Another class of oral malodour control agents include absorbents. These are used to absorb, adsorb, bind or otherwise complex the volatile oral malodour materials. Examples of such agents include talc, mushroom extract, zeolite, cyclodextrin, silica shell and mixtures thereof. Such materials are preferably used at a level of from about 0.5% to about 10%, preferably from about 1% to about 5%, by weight of the composition.

H-2 Antagonists: Histamine-2 (H-2) receptor antagonist compounds (H-2 antagonists) may be used in the oral care compositions of the present invention. As used herein, selective H-2 antagonists are compounds that block H-2 receptors, but do not have meaningful activity in blocking histamine -1 (H-1) receptors. Selective H-2 antagonists include those disclosed in U.S. Pat. Nos. 5,294,433 and 5,364,616 Singer et al., issued Mar. 15th 1994 and Nov. 15th 1994 respectively and assigned to Procter & Gamble, wherein the selective H-2 antagonist is selected from the group consisting of cimetidine, etintidine, ranitidine, ICIA-5165, tiotidine, ORF-17578, lupititidine, donetidine, famotidine, roxatidiein, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728 and HB-408.4. Particularly preferred is cimetidien (SKF-92334), N-cyano-N'-methyl-N"-(2-(((5-methyl-1H-imidazol-4-yl)methyl)thio)ethyl)guanidine:

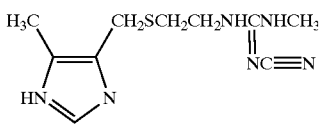

Cimetidine is also disclosed in the Merck Indes, 11th editions (1989), p354 (entry no 2279), and Physicians' Desk Reference, 46th edition (1992), p2228. Related preferred H-2 antagonists include burimamide and metiamide. Again it is believed that an enhanced synergistic effecti is achieved by using the natural extracts disclosed herein in combination with the H2 antagonists. This is because whilst the antagonist acts to reduce inflammation the extract is able to have an anti-bacterial effect in reducing the level of infection. Thus by use of the two together more effective reduction in disease is achieved than by using either alone.

Water

Compositions of the present invention comprise less than about 10%, preferably less than about 8%, more preferably less than about 5%, even more preferably less than about 3%, and most preferably less than about 2%, by weight of the composition, water. The low levels of water are required in order to ensure that the polyphenol components of the plant extracts are not oxidised and, if included, any long chain polyphosphates are not hydrolysed in the final composition.

Water used in the preparation of commercially suitable compositions should preferably be of low ion content and free of organic impurities. The amount of water in a composition should be considered to be not only that added as free water, but also water which is introduced with other materials, such as with sorbitol, silica, surfactant solutions and/or colour solutions. Furthermore the amount of water should be considered by weight of the final composition as a whole including coat and/or filling, where appropriate.

Confectionery Carrier Material

Compositions of the present invention are confectionery compositions including chewing gum. Suitable physical forms include sticks, dragees, chicklets, and batons. Although the exact ingredients for each product form will vary from product to product, the specific techniques will be known by one skilled in the art. However there are some general ingredients which are common to all product forms and these are discussed in more detail below. Preferred product forms are pressed tablets, low boiled candy, hard boiled candy and chewing gum which are readily formulated with less than about 10%, by weight of the composition, water.

Confectionery compositions of the present invention comprise a carrier material. The carrier materials vary depending on the type of confectionery used and would be well known to one skilled in the art. The carrier material can be chosen from chewable or non chewble materials. It is referred that the compositions comprise at least 10% chewable material. The chewable material can be selected from gums including agar agar gum, gelatine etc; low boiled sugar candy base and gum base materials. It is preferred that the carrier material for compositions of the present invention are not in the form of a whippable or aerated emulsion. Hard and low boiled candy carrier, pressed tablets and the like usually comprise greater than about 70% bulk sweetener including suitable sugar and sugar syrups including cariogenic and non-cariogenic materials. Low boiled candies can also comprise butter to form chewable toffee. For jelly and gum drop compositions the carrier comprises greater than about 25% bulk sweetener and additionally comprise gums including gum arabic, gelatine, agar agar powder and the like.

Compositions of the present invention are preferably in the form of a chewing gum. As such it is preferred that the compositions comprise greater than about 10%, preferably greater than about 15%, more preferably greater than about 20% and most preferably greater than about 25% and up to about 75%, by weight of the composition, of gum base. The gum base comprises a carrier material, or mixture of carrier materials, selected from elastomers, resins or waxes. The gum base carrier materials are water insoluble materials which are typically not released in the mouth. Such materials include:

(i) Elastomers and Elastomer Solvents

Compositions of the present invention preferably comprise an elastomer, or mixture of several different elastomers. Elastomeric materials are generally known in the art but illustrative examples include styrene-butadiene rubber (SBR); synthetic gums; polyisobutylene and isobutylene-isoprene copolymers; natural gums; chicle; natural rubber; jelutong; balata; guttapercha; lechi caspi; sorva; and mixtures thereof. Compositions of the present invention preferably comprise from about 2% to about 30%, more preferably from about 5% to about 25%, by weight, of elastomer. These levels are determined by the desired final texture of the chewing gum since when the total level of elastomer is below about 2% the base composition lacks elasticity, chewing texture, and cohesiveness whereas at levels above about 30% the formulation is hard, rubbery and maintains a tight chew.

Elastomer solvents are also preferably present in compositions of the present invention since they aid softening of the elastomer component. Preferred examples of elastomer solvents for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. Compositions of the present invention preferably comprise from about 2% to about 50%, more preferably from about 10% to about 35%, by weight, of elastomer solvent.

(ii) Resins and Waxes

Resins are an optional, but desirable, ingredient of chewing gum compositions herein. They serve to plasticise the gum base. Suitable resins include polyvinyl acetate (PVA); terpene resins, including polyterpene and polymers of alpha-pinene or beta-pinene; and mixtures thereof. Such compositions preferably comprise from about 3% to about 25%, preferably from about 5% to about 20%, by weight, of resin.

The chewing gum compositions may also include one or more waxes. Suitable waxes include paraffin wax; microcrystalline wax; Fischer-Tropsch paraffin; natural waxes such as candellilla, carnauba and beeswax; polyolefin waxes such as polyethylene wax; and mixtures thereof. Compositions comprise up to about 25%, preferably from about 5% to about 20%, by weight, of wax.

Confectionery compositions of the present invention can be centre filled. Such products preferably comprise from about 60% to about 95%, more preferably from about 75% to about 85% of an edible shell and from about 5% to about 40%, preferably from about 15% to bout 25%, by weight of the composition, of an edible filling. It is possible that centre filled confectionery composition can comprise an oral care active in the edible shell and or a different oral care active, or mixture of actives, in the edible filling. In addition the composition can comprise different flavouring agents in the shell and the filling.

Compositions of the present invention may comprise one or more crunchy solid particles dispersed throughout the carrier material. The crunchy preferably particle has a minimum particle size such that the particles are retained by a 0.1 mm mesh, preferably a 0.112 mm mesh, more preferably a 0.16 mm mesh, even more preferably a 0.18 mm mesh and most preferably a 0.2 mm mesh wherein the meshes are selected from the DIN 4188 mesh series. Furthermore the particle preferably has a maximum particle size such that it passes through a 2 mm mesh, preferably a 1 mm mesh, more preferably an 0.8 mm mesh, even more preferably a 0.5 mm mesh and most preferably a 0.4 mm mesh, again wherein the meshes are selected from the DIN 4188 mesh series. The solubility of the particle is preferably at least 1 g per 100 ml at 25° C., more preferably at least 5 g, even more preferably at least 8 g and most preferably at least 15 g per 100 ml at 25° C. Finally it is preferred that the particulate material has a hardness of greater than 1, preferably greater than 2 on the Mohs hardness scale. The particle size, solubility and hardness properties confer a crunchy texture to the confectionery itself. Such particles can be present as solid forms of one of the oral care actives outlined above, in the case where the oral care active is a solid, or can be a further particle such as sugar crystals, dried fruits, nuts, etc. The crunchy texture can be used to reinforce the oral care benefits to the consumer. Different crunchy textures can be obtained by milling the particles to the desired size or by blending different commercial grades of particles to achieve the desired crunch. It is preferred the that crunchy sensation remains consumer noticeable for at least 1 minute 30 seconds, preferably for at least 2 minutes and more preferably for at least 2 minutes 30 seconds. However it is also preferred that the crunchy texture has disappeared by 5 minutes, preferably by 4 minutes so that the material does not abrade the dentin or so that the product does not have a gritty residue.

Furthermore the confectionery compositions of the present invention can also be coated. The outer coating may be hard or crunchy. Typically, the outer coating will essentially consist of sorbitol, maltitol, xylitol, isomalt, and other crystallisable polyols. Furthermore the coating will typically consist of several opaque layers, such that the confectionery core is not visible through the coating itself, which can optionally be covered with a further one or more transparent layers for aesthetic, textural and protective purposes. The outer coating may also contain small amounts of water and gum arabic. A polyol coating can be further coated with wax. The coating is applied in a conventional manner by successive applications of a coating solution, with drying in between each coat, as described in WO99/44436. As the coating dries it usually becomes opaque and is usually white, though other colorants may be added. A polyol coating can be further coated with wax. The coating can further comprise coloured flakes or speckles. If the composition comprises a coat it is possible that one or more of the oral care actives can be dispersed throughout the coat. This is especially preferred if one or more oral care active is incompatible in a single phase composition with another of the actives.

Balance of the Composition

Compositions of the present invention preferably comprise safe and effective levels of one or more additional components. Such materials are well known and are readily chosen by one skilled in the art based on the oral care, physical and aesthetic properties desired for the compositions being prepared. Examples of such materials include, but are not limited to fats, solvents, waxes, emulsifiers, softeners, bulking agents, cationic material, buffers, whitening agents, alkali metal bicarbonate salts, thickening materials, humectants, water, surfactants, titanium dioxide, flavouring agents, colouring agents, and mixtures thereof. Those ingredients most commonly used are described in more detail below.

Antioxidants

Antioxidants are generally recognised as useful in compositions such as those of the present invention. Antioxidants are disclosed in texts such as Cadenas and Packer, The Handbook of Antioxidants, © 1996 by Marel Dekker, Inc. Antioxidants that may be included in the oral care compositions of the present invention include, but are not limited to, Vitamin E, ascorbic acid, Uric acid, carotenoids, Vitamin A, flavenoids and polyphenols, herbal antioxidants, melatonin, aminoindoles, lipoic acids and mixtures thereof.

Teeth Colour Modifying Substances

Teeth colour modifying substances may be considered among the oral care actives useful in the present invention. These substance are suitable for modifying the colour of the teeth to satisfy the consumer such as those listed in the CTFA Cosmetic Ingredient Handbook, $3^{rd}$ Edition, Cosmetic and Fragrances Association Inc., Wash. D.C. (1982), incorporated herein by reference. Specific examples include talc, mica, magnesium carbonate, calcium carbonate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical pigment levels from about 0.05% to about 20%, preferably from about 0.1% to about 15% and most preferably from about 0.25% to about 10%, by weight, of the composition.

Compositions for use herein may also comprise materials that remove or bleach intrinsic or extrinsic stains on or in tooth surfaces. Such substance are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. Additional bleaching substances may be hypochlorite, and chlorine dioxide. A preferred percarbonate is sodium percarbonate. Preferred persulphates are oxones. The level of these substances is dependent on the available oxygen or chlorine. This level is generally used in compositions of the present invention at levels from about 0.1% to about 35%, preferably from about 1% to about 25% and most preferably from about 5% to about 10%, by weight of the composition.

Nutrients

Nutrients may improve the condition of the oral cavity and can be included in the oral care compositions or substances of the present invention. Nutrients include minerals, vitamins, oral nutritional supplements, enteral nutritional supplements, herbal supplements, natural extracts and mixtures thereof as disclosed in Drug Facts and Comparisons (loose leaf drug information service), Wolters Kluer Company, St Louis, Mo., © 01997. Minerals that can be included with the compositions of the present invention include calcium, phosphorus, fluoride, zinc, manganese, potassium and mixtures thereof. Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Fish oil contains large amounts of Omega-3 (N-3) polyunsaturated fatty acids, eicosapentaenoic acid and docosahexaenoic acid.

Sweeteners

Two main types of sweeteners exist; bulk sweeteners and high intensity sweeteners. In general, the amount of sweetener used will vary depending on the sweetener and the overall desired aesthetics but levels used should be high enough such that the desired level of sweetness is achieved independent from the flavour. When bulk sweeteners are used they can also assume the role of the bulking agent or filler within the composition.

Bulk Cariogenic Sweetener: Compositions of the present invention may comprise sweetener materials. Such materials include monosaccharides, disaccharides, polysaccharides and mixtures thereof. Examples include xylose, ribose, glucose, mannose, galactose, fructose, dextrose, sucrose, sugar maltose, fructo oligo saccharide syrups, partially hydrolysed starch, or corn syrup solids and mixtures thereof. However, such materials can often lead to the formation of cavities since they are readily metabolised by bacteria and other micro-organisms in the oral cavity. It is preferred that compositions of the present invention comprise less than about 10%, preferably less than about 5%, more preferably less than about 2%, even more preferably less than about 1%, and most preferably less than about 0.5%, by weight of the composition, of cariogenic sweetener. If desired the composition can comprise 0% cariogenic sweetener.

Bulk Non Cariogenic Sweeteners: Compositions of the present invention preferably comprise a non-cariogenic sweetener. As used herein the term "non-cariogenic" refers to sweeteners which are not able to be metabolised by oral microbes and therefore do not contribute to the formation of dental caries. It is preferred that compositions of the present invention comprise greater than about 10%, preferably greater than about 20%, more preferably greater than about 30% and most preferably greater than about 40%, by weight of the composition, of non cariogenic sweetener. Compositions of the present invention can comprise up to 99% of non cariogenic sweetener.

Preferred bulk non cariogenic sweetening agents are sugar alcohols such as sorbitol, xylitol, mannitol, maltitol, isomalt, hydrogenated starch hydrolisate, insulin, and other non-carigenic edible polyols such as glycerin and erythritol and mixtures thereof. Most preferred are non cariogenic sweeteners selected from the group consisting of maltitol, mannitol, xylitol, sorbitol, sucralose, aspartame and its salts, and mixtures thereof. In general compositions comprise from about 10% to about 80%, more preferably from about 30% to about 70%, by weight, of bulk sweetener.

High Intensity Sweeteners: High intensity sweeteners are preferred over bulk sweeteners for use in compositions of the present invention because, for among other reasons, high intensity sweeteners may prolong the flavour of the finished gum composition during chewing. Suitable high intensity sweeteners include: dipeptide based sweeteners such as L-aspartyl-L-phenylalanine methyl ester (Aspartame) and equivalents (described in U.S. Pat. No. 3,492,131), L-α-aspartyl-N-(2,2,4,4-tetramethyl-3-thietanyl)-D-alaninamide hydrate (Alitame) and the like; saccharin and its soluble salts eg sodium or calcium saccharin salts; cyclamate salts for example acesulfame-K and the like, chlorinated derivatives of sucrose such as chlorodeoxysucrose and the like; and protein based sweeteners, such as Thaumatin (talin). Compositions of the present invention preferably comprise from about 0.01% to about 2.0%, more preferably from about 0.05% to about 0.5%, by weight, of high intensity sweetener.

Additional Chewing Gum Ingredients

There are several ingredients which are commonly added to chewing gum compositions and which are not commonly used in other types of confectionery. Examples of materials are listed below but this list is not to be considered limiting. Similarly such ingredients can be used in other types of confectionery if desired.

Chewing gum compositions of the present invention may also comprise plasticisers in addition to the resin component. Suitable plasticisers include glyceryl triacetate, acetylated monoglyceride, glyceryl tributyrate, ethyl laurate, ethyl acetoacetate, diethyl tartrate, ethyl or butyl lactates, diethyl malate, ethyl oleate, castor oil, succinylated monoglycerides or mixtures thereof. Glyceryl triacetate and acetylated monoglyceride are preferred. Compositions preferably comprise up to about 10%, preferably from about 0.1% to about 3%, by weight, of plasticiser.

Compositions of the present invention preferably comprise a softener or mixture of softeners which, when incorporated into the gum base, assist in modifying the texture and consistency properties. In particular, they help to soften the chew and to maintain chew softness over an extended period of time. Suitable softeners include fatty materials such as lanolin, stearic acid, sodium stearate and potassium stearate; polyhydric alcohols such as glycerine, propylene glycol, and the like; and mixtures thereof. Compositions preferably comprise up to about 30%, more preferably from about 0.1% to about 10%, by weight, of softener. In a preferred embodiment, the chewing gum composition comprises from about 0.1% to about 10%, by weight, of a fatty softener selected from stearic acid, sodium stearate, potassium stearate and mixtures thereof, preferably stearic acid.

The chewing gum compositions preferably comprise an emulsifier such as glycerol monostearate, lecithin, fatty acid monoglycerides, diglycerides, propylene glycol monostearate and mixtures thereof. Compositions comprise up to about 10%, and preferably from about 2% to about 6%, by weight, of emulsifier.

Various fats can also be included in the chewing gum compositions of the present invention. Preferred fats include the hydrogenated vegetable oils such as hydrogenated palm oil, hydrogenated soybean oil, hydrogenated cotton seed oil and various other hydrogenated vegetable oils and mixtures thereof. The fats can suitably be used at a level up to about 20%, preferably from about 1% to about 10%, by weight, of the chewing gum composition.

Bulking Agents

Bulking agents, such as fillers, can also be employed in confectionery. Suitable fillers and bulking agents are generally non-abrasive, preferably with an average particle size less than 5 μm, more preferably less than 3 μm and especially less than 1 μm. Illustrative bulking agents include calcium carbonate or ground limestone, talc, aluminium hydroxide, alumina, aluminium silicates, dicalcium phosphate and mixtures thereof Compositions preferably comprise up to about 50%, more preferably up to about 30%, and most preferably up to about 10%, by weight, of bulking agent.

Flavouring Agents

Compositions of the present invention can preferably comprise a flavouring agent. As used herein the term "flavouring agent" means those flavour essences and equivalent synthetic materials which are added to flavour the composition. The flavouring agent can also include specific materials which are added to provide a warming or cooling sensation.

Flavouring agents are well known in the art. They include synthetic flavours and or oils and or essences derived from plants, roots, beans, nuts, leaves, flowers, fruits and so forth and mixtures thereof. Examples of suitable flavours include lemon, orange, banana, grape, lime, apricot, grapefruit, apple, strawberry, cherry, chocolate, pineapple, coffee, cocoa, cola, peanut, almond, liquorice, cinnamon and the like. The amount of flavouring agent employed is normally a matter of preference but in general they are used in amounts up to about 4%, preferably from about 0.1 to about 1%, by weight of the composition.

Compositions of the present invention can optionally comprise a cooling agent and suitable materials are described in WO 97/06695. Preferred for use herein are physiological cooling agents selected from the group consisting of menthol, peppermint oil, N-substituted -p-menthane-3-carboxamides, acyclic tertiary and secondary carboxamides, 3-1-methoxy propan-1,2-diol and mixtures thereof. Particularly preferred are menthol and menthol containing oils such as peppermint oil. Cooling agents are preferably used at a level of from about 0.001 to about 5%, more preferably from about 0.05% to about 3.5%, by weight of the composition.

Compositions of the present invention can optionally comprise a warming agent. Preferred agents include those selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isamyl ether, vanillyl alcohol n-hexyl ether, vanillyl alcohol methyl ether, vanillyl alcohol ethyl ether, ginerol, shogaol, paradol, zingerone, capsaicin, dihydrocapsaicin, nodihydrocapsaicin, homocapsaicin, homodihydrocapsaicin, ethanol, isopropyl alcohol, iso-amylalcohol, benzyl alcohol, chloroform, eugenol, cinnamon oil, cinnamic aldehyde, and mixtures thereof. Warming agents are preferably used at a level of from about 0.001 to about 5%, more preferably from about 0.05% to about 3.5%, by weight of the composition.

Preparation of Compositions

The compositions of the present invention are prepared by standard techniques well known to those skilled in the art. If the composition comprises more than one phase, in general the different phases will be prepared separately, with materials of similar phase partitioning being added in any order. The two phases will then be combined with vigorous stirring to form the multiphase system eg an emulsion or dispersion. Any ingredients in the formulation with high volatility, or which are susceptible to hydrolysis at high temperatures, will usually be added post mixing of the different phases with gentle stirring. If the composition optionally comprises polyphosphate it is preferred that the polyphosphate is not pre-dispersed in water prior to addition to the composition in order to prevent hydrolysis. It is therefore preferred that the polyphosphate be added as a solution. Typical confectionery methods are highly suitable for manufacturing of compositions of the present invention. Finally if the products are coated the coating step is conducted as a final step. The coating can be applied by panning or spray dried techniques commonly known to those skilled in the art.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope. Unless otherwise indicated, all ingredients are expressed as a weight percentage of the composition.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

| INGREDIENT | I % w/w | II % w/w | III % w/w | IV % w/w | V % w/w | VI % w/w | VII % w/w | VIII % w/w |
|---|---|---|---|---|---|---|---|---|
| Sugar | 56.99 | — | 44.16 | 31.78 | — | — | — | 93.40 |
| Glucose | 38.00 | — | 40.40 | 21.19 | — | — | — | — |
| Gumbase | — | — | — | 30.00 | 28.00 | 28.00 | 28.00 | — |
| Sorbitol | — | — | — | — | 42.42 | 33.42 | 42.42 | — |
| Xylitol | — | — | — | — | 20.00 | 20.00 | 20.00 | — |
| Isomalt | — | 90.95 | — | — | — | — | — | — |
| Glycerin | — | — | — | 8.00 | 5.00 | 5.00 | 5.00 | — |
| Vegetable fat | — | — | 5.00 | — | — | — | — | — |
| Gum arabic | — | — | 0.12 | — | — | — | — | — |
| Gelatine | — | — | 0.12 | — | — | — | — | 0.10 |
| Water | 3.00 | 3.00 | 8.00 | 0.50 | 0.50 | 0.50 | 0.50 | 0.50 |
| Gold Thread extract | 0.50 | — | — | — | 0.50 | — | — | — |
| Honeysuckle extract | — | 1.00 | — | — | — | 0.50 | — | — |
| Green tea | — | — | 1.00 | — | — | — | 1.00 | — |

-continued

| INGREDIENT | I % w/w | II % w/w | III % w/w | IV % w/w | V % w/w | VI % w/w | VII % w/w | VIII % w/w |
|---|---|---|---|---|---|---|---|---|
| extract | | | | | | | | |
| Magnolia Extract | — | — | — | 0.50 | — | — | — | — |
| Eucalyptol | — | — | — | 0.50 | — | — | 0.50 | — |
| Cetyl pyridinium chloride | — | — | 0.10 | — | — | — | — | — |
| Sodium polyphosphate | 5.00 | — | — | 5.00 | 1.00 | 10.00 | — | 5.00 |
| Flavour | 1.00 | 1.00 | 1.00 | 2.50 | 2.50 | 2.50 | 2.50 | 1.00 |
| Lecithin | — | — | 0.10 | 0.03 | 0.03 | 0.03 | 0.03 | — |
| Acesulfam K | — | 0.05 | — | — | 0.05 | 0.05 | 0.05 | — |
| TOTAL | 100.00 | 100.00 | 100.00 | 100.00 | 100.00 | 100.00 | 100.00 | 100.00 |
| COATING (20–30% w/w) | | | | | | | | |
| Sorbitol | — | — | — | — | — | 94.80 | 94.80 | — |
| Water | — | — | — | — | — | 2.00 | 2.00 | — |
| Titanium Dioxide | — | — | — | — | — | 1.50 | 1.50 | — |
| Acesulfam K | — | — | — | — | — | 0.05 | 0.05 | — |
| Polysorbate 60 | — | — | — | — | — | 0.15 | 0.15 | — |
| Flavour | — | — | — | — | — | 1.50 | 1.50 | — |
| TOTAL | — | — | — | — | — | 100.00 | 100.00 | — |

Examples I & II

Hardboiled candy. Sugar (or Isomalt) is dissolved in water and heated under stirring to 110–112° C. Glucose syrup is then added and the mix heated to 141–142° C. to boil off water. Batch is drawn down under vacuum and polyphosphate/flavours added at approx 90° C. in low humidity environment. Batch is folded on a hot table and subsequently cooled on cold table (20° C.) prior to transfer to the batch forming and die cutting apparatus. Final product has a Glass like translucent appearance.

Example III

Low boiled candy: Isomalt is slowly dissolved in water to 80° C. and subsequently cooked to 118–130° C. at which point the heating is removed. Fat is added 2–3° C. lower than this final cook temperature. Gelatine, flavours, acid and polyphosphate are added after cooking has ended following which the final products are formed.

Examples IV–VII

Chewing gums: Melt gumabse to 55–60° C. in sigma blade mixer. Add in bulk sweetener and glycerin, mix. Add in actives and extract and mix. Mix in flavour last. Remove from heat and allow to cool before moulding and cutting. Coating pre-solution is sprayed onto cooled gum in fine layers which are allowed to dry before subsequent layers are added. Sufficient coating is added such that total coating weight is 20–30% of final finished pellet weight.

Example VIII

Compressed mint. A pre-formed solution of gelatine and gum products is prepared and sprayed over sugar or dextrose or isomalt to form a granular mixture. This is dried and sieved and subsequently compressed to form tablets.

What is claimed is:

1. A confectionery composition comprising:
   (i) an effective amount of a natural plant extract selected from the group consisting of tea, gold thread, honeysuckle, magnolia extracts and mixtures thereof;
   (ii) a polyphosphate oral care active;
   (iii) less than about 10% by weight water; and
   (iv) a confectionery carrier material, which is a chewing gum base.

2. The composition of claim 1 wherein the extract is a green tea extract, a magnolia extract and mixtures thereof.

3. The composition of claim 1 wherein the extract comprises greater than about 1%, by weight of the extract, of polyphenol.

4. The composition of claim 3 wherein the extract comprises greater than about 15%, by weight of the extract, of polyphenol.

5. The composition of claim 1 wherein the extract is obtained by solvent extraction and wherein the solvent used for extraction is selected from the group consisting of alcohols, water, acetone, ethyl acetate, glycerol, diethyl ether, propylene glycol and mixtures thereof.

6. The composition of claim 2 wherein the composition comprises from about 0.001% to about 15%, by weight of the composition, of the extract.

7. The composition of claim 6 wherein the composition comprises from about 0.1% to about 5%, by weight of the composition, of the extract.

8. The composition of claim 1 wherein the composition comprises from about 0.1% to about 15%, by weight of the composition, of polyphosphates.

9. The composition of claim 8 wherein the oral care active is polyphosphate having an average anion chain length of from about 3 to about 40.

10. The composition of claim 9 wherein the oral care active is polyphosphate having an average anion chain length of from about 18 to about 25.

11. The composition of claim 10 wherein the polyphosphate is an alkali metal salt.

12. The composition of claim 1 wherein the composition comprises greater than about 10%, by weight of the composition, of gum base.

13. The composition of claim 1 wherein the composition comprises less than about 8%, by weight of the composition, water.

14. The composition of claim 13 wherein the composition comprises less than about 2%, by weight of the composition, water.

15. The composition of claim 1 wherein the composition comprises greater than about 10%, by weight of the composition, of a non cariogenic sweetener selected from the group consisting of maltitol, mannitol, xylitol, sorbitol, sucralose, aspartame and mixtures thereof.

16. The composition of claim 1 wherein the confectionery composition has an outer coating.

17. The composition of claim 16 wherein the oral care active is dispersed throughout the coating.

* * * * *